(12) United States Patent
Butterfield

(10) Patent No.: US 10,864,007 B2
(45) Date of Patent: Dec. 15, 2020

(54) ABRADING DEVICE AND METHOD FOR CREATING ABRASIONS ON A MEMBRANE

(71) Applicant: Keith Butterfield, Portland, ME (US)

(72) Inventor: Keith Butterfield, Portland, ME (US)

(*) Notice: Subject to any disclaimer, the term of this patent is extended or adjusted under 35 U.S.C. 154(b) by 383 days.

(21) Appl. No.: 14/690,960

(22) Filed: Apr. 20, 2015

(65) Prior Publication Data

US 2016/0302813 A1  Oct. 20, 2016

(51) Int. Cl.
   *A61B 17/32*  (2006.01)
   *A61B 17/00*  (2006.01)

(52) U.S. Cl.
   CPC ............... *A61B 17/320016* (2013.01); *A61B 2017/00809* (2013.01); *A61B 2017/00836* (2013.01); *A61B 2017/00946* (2013.01); *A61B 2017/320012* (2013.01)

(58) Field of Classification Search
   CPC ............ A61B 17/32; A61B 17/320016; A61B 17/32002; A61B 2017/00809; A61B 2017/320004; A61B 2017/320008; A61B 2017/320012; A61B 2017/320028; A61B 2017/320032
   See application file for complete search history.

(56) References Cited

U.S. PATENT DOCUMENTS

| | | | | | |
|---|---|---|---|---|---|
| 5,370,653 A | * | 12/1994 | Cragg | .................... | A61B 17/22 600/569 |
| 5,681,335 A | * | 10/1997 | Serra | .................. | A61B 17/3207 606/159 |
| 5,702,413 A | * | 12/1997 | Lafontaine | ............. | A61B 17/22 606/159 |
| 6,346,074 B1 | * | 2/2002 | Roth | ................ | A61B 17/00234 600/121 |
| 2014/0088459 A1 | * | 3/2014 | Roush | ............... | A61M 25/0032 600/569 |

FOREIGN PATENT DOCUMENTS

FR  2981840 A1 *  5/2013  ............. A61B 17/00

* cited by examiner

*Primary Examiner* — Todd J Scherbel
(74) *Attorney, Agent, or Firm* — J. Wiley Horton

(57) ABSTRACT

An abrading device and method for irritating and blotting a membrane, particularly the pleural membrane. The method uses a device which is small enough to be inserted and withdrawn through a thoracoport. The device includes a proximal end configured to be gripped by a surgeon and a distal end configured to be inserted into the patient. A stainless steel shaft connects the distal and proximal ends of the abrading device. The distal end includes a series of nylon bristles. The bristles are attached to the device wire wrapped around the distal end of the device. The connecting shaft and wrapped wire are malleable. Once the device is inserted, the surgeon grips the proximal end and manipulates the device so that the series of nylon bristles abrades the walls of the pleural space. Once the abrading process is complete, the surgeon can easily withdraw the device back through the thoracoport.

15 Claims, 9 Drawing Sheets

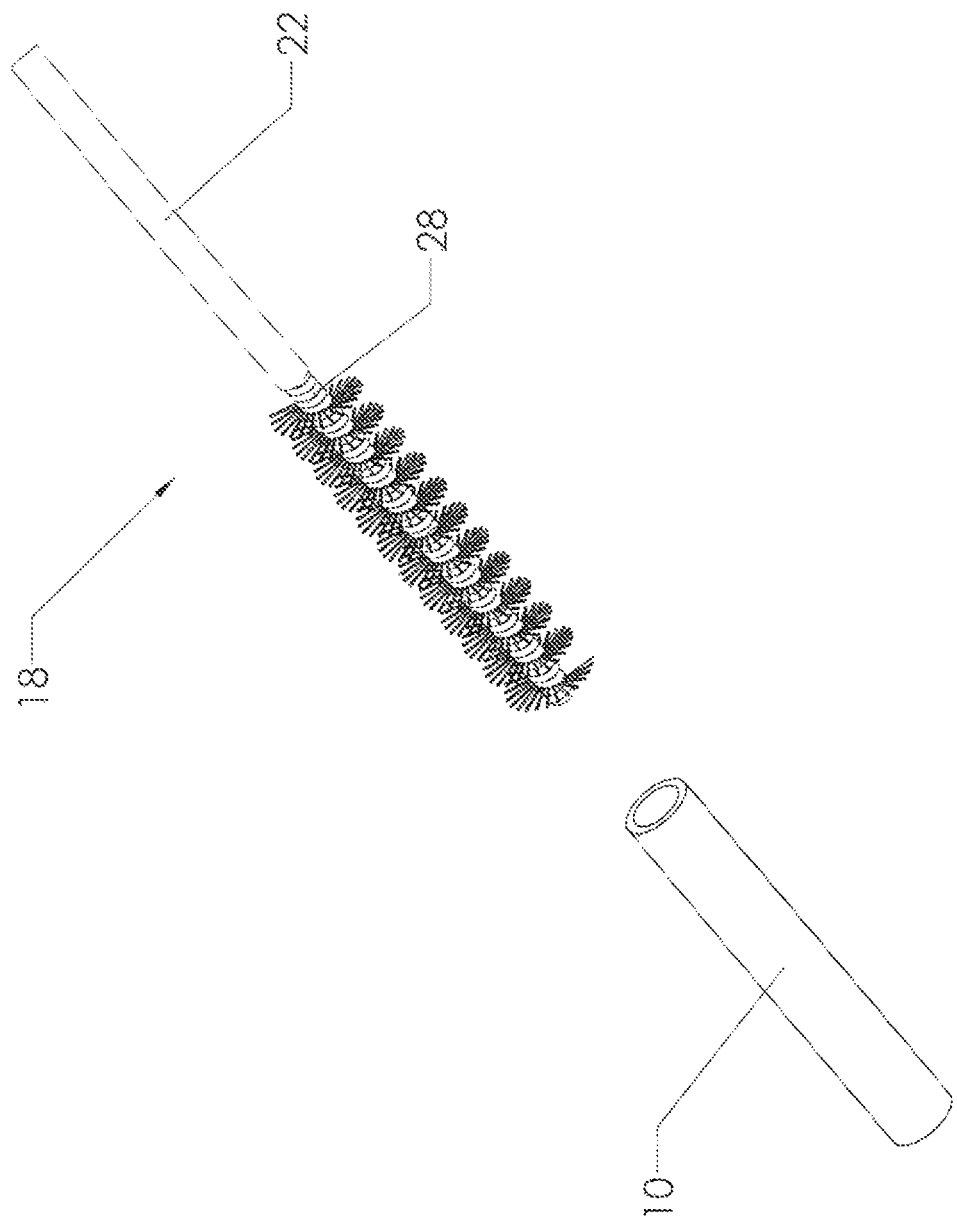

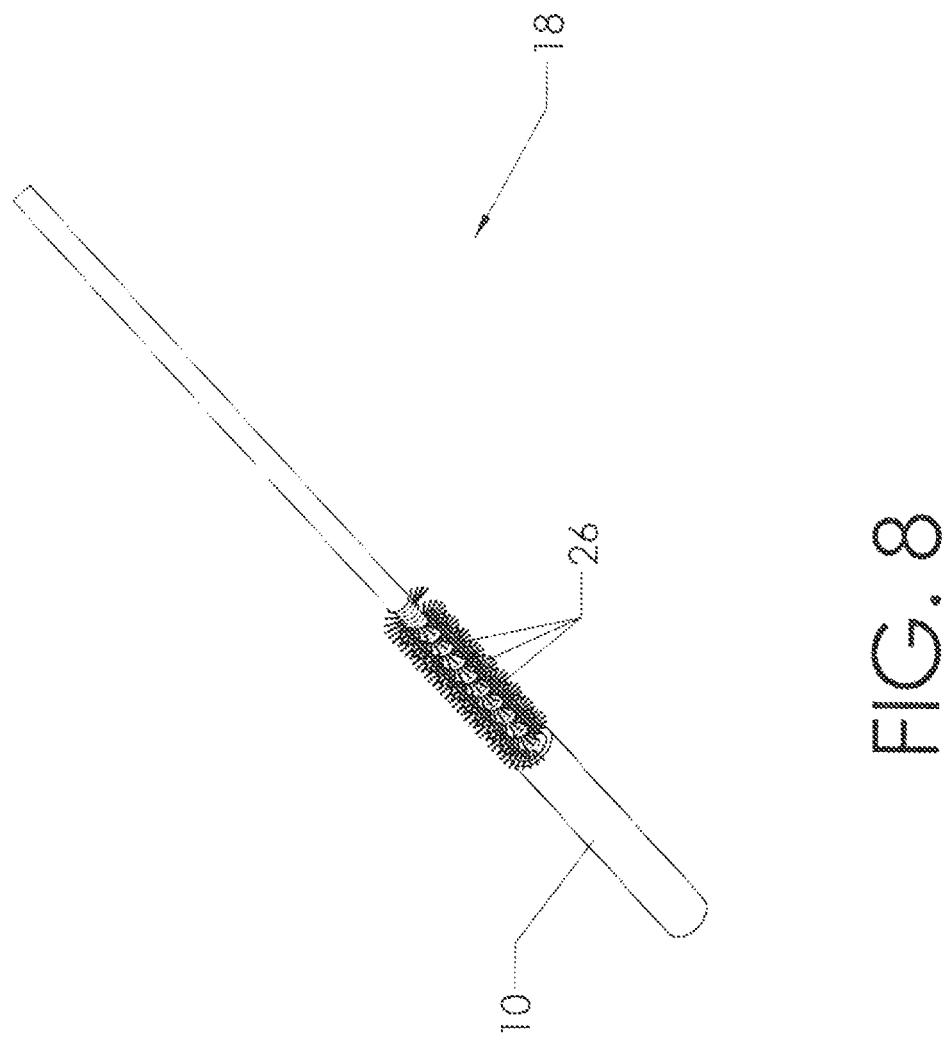

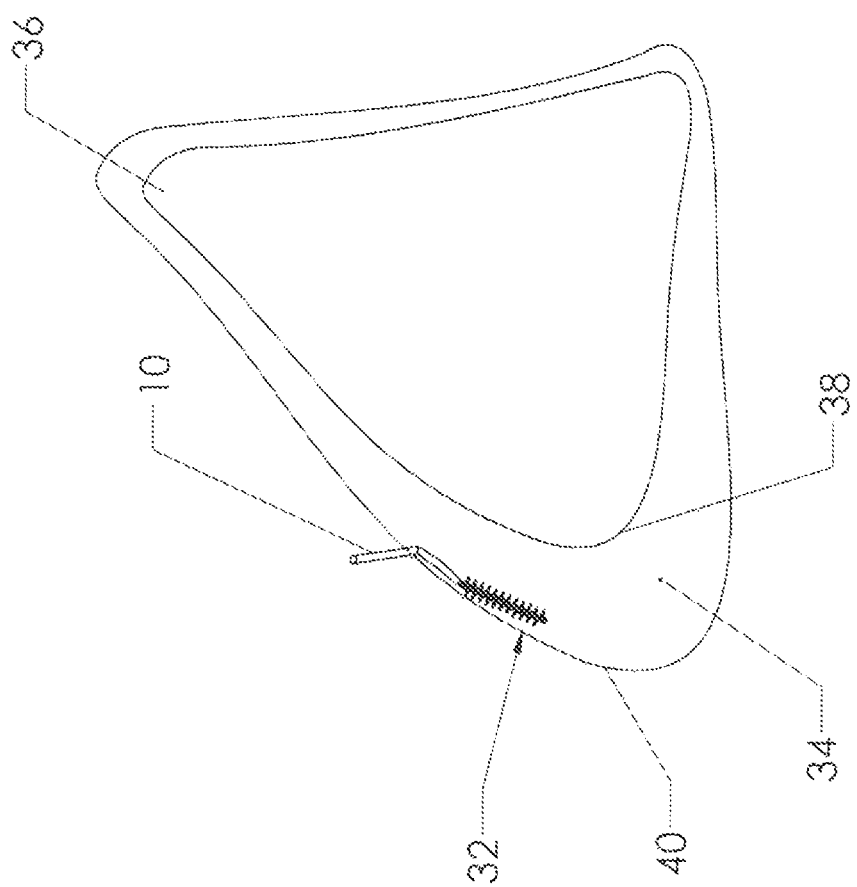

ABRADING DEVICE AND METHOD FOR CREATING ABRASIONS ON A MEMBRANE

CROSS-REFERENCES TO RELATED APPLICATIONS

Not Applicable

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of surgical devices. More specifically, the invention comprises a method for creating abrasions on a membrane, such as the pleural membrane using an abrading device.

2. Description of the Related Art

Pleurodesis is a medical procedure in which the pleural space between the chest wall and the lung of a patient is obliterated. This is commonly done in order to prevent the recurrence of pneumothorax or pleural effusion. Pleurodesis is accomplished by irritating the parietal pleura (outer pleura attached to the chest wall), thereby creating abrasions on the chest wall, which causes adhesion between the wall and the lung of the patient. Sealing off of the pleural space prevents unwanted fluid or air from entering and occupying the area after the surgery.

Pleurodesis is typically performed during a thoracotomy or thoracoscopy. Both surgical techniques are used to enter the chest to perform any number of different medical procedures. The difference between the two techniques is related to the size of the incision that is made in the patient. The incision for a thoracotomy is made on the side of the patient's chest and is typically four to six inches long. In a thoraeoseopic operation several small incisions, generally ¼ to 1 inch in diameter, are made in different places around the chest.

FIG. 2 shows a prior art thoracoport 10 with a thoracoscope 12 inserted through the thoracoport 10. Thoracoports 10, small tubes or pipe structures, are typically placed into the small incisions through the chest wall to allow for easy insertion of other small instruments, thereby reducing the risk of damage to surrounding tissues during insertion and withdrawal. A thoracoscope 12, or small optical camera, is inserted through at least one of the thoracoports 10 to view the inside of the chest. This minimally invasive operation allows surgeons to have maximum mobility inside the chest without putting pressure on the ribs. It also allows a surgeon to enter and exit the chest with little trauma to the nerves that travel along the bottom edge of each rib. The benefits to patients include reduced post-operative pain, a faster recovery and less scarring.

Upon nearing the end of a thoracotomy or a thoracoscopy, a surgeon would typically perform surgical pleurodesis by irritating the pleural membrane with a rough pad. FIG. 1 illustrates the existing equipment used for this process. Surgeons attach prior art gauze 16 to prior art Kelly clamp 14 and physically rub the rough pad, gauze or other abrasive material (oftentimes this is whatever the surgeon can find) along the pleural membrane. Those familiar with the art will realize that gauze 16 may be many abrasive materials, including electrocautery cleaning pads which contains aluminum oxide. When these cleaning pads are used, aluminum oxide can be left in the chest cavity of the patient. Kelly clamp 14 is a medical tool that resembles a pair of scissors; however, the blade is replaced by a locking clamp. A surgeon using a Kelly clamp 14 during a thoracotomy would typically have to disturb the incision site and surrounding tissue in order to push the abrasive gauze 16 into the patient's body between the chest wall and lung. This causes an increase in trauma to the surrounding tissue and likely extension of the initial incision site. Additionally, it is difficult to view the tissue that is being irritated, as the insertion of the Kelly clamp 14 blocks the surgeon's view.

Performing surgical pleurodesis at the end of a thoracoscopy is more difficult than in the thoracotomy. Because the incisions are small, a surgeon must stretch the incision site to fit the Kelly clamp 14 down into the pleural membrane. Again, the result is increased trauma, likely incision extension and difficulty in viewing the irritation process. Since the incision site is so small the reader will note that the insertion of the Kelly clamp 14 and rough gauze 16 is difficult and likely causes more trauma to the body than would be caused when working with a larger incision site.

In addition to increased trauma to the incision site, Kelly clamp 14 (or other clamping devices) must be either tightened in order to clamp gauze 16 or the surgeon may need to maintain a firm grasp on clamp 14. In either situation, it is possible for gauze 16 to disengage from clamp 14, thereby becoming suspended freely within the patient. This increases the duration of the surgical procedure, may cause further complications such as the spreading of cancer cells from diseased lung tissue into the incision site tissue, and may further irritate the incision site. Currently, there is not an adequate medical device that is designed for assisting thoracic surgeons with a mechanical pleurodesis procedure. Thus, different surgeons concoct their own tool by using different graspers and different configurations of clenching the gauze within the jaws which affect the repeatability these procedures and of the outcomes of the surgery. While graspers or clamps 14 are used for many surgical procedures, clamp 14 is not ideal for surgical pleurodesis. In fact, when using Kelly clamp 14 the surgeon risks puncturing or otherwise severing other thoracic organs or tissues. In addition, it is common for surgeons to unintentionally drop gauze 16 while performing pleurodesis, thereby causing the surgeon to find and remove gauze 16 and increasing the duration of the procedure.

Abrading devices have not previously been small enough to fit through a throacoport or other small opening. Additionally, the abrading surface, usually a rough pad, has not previously been retractable into a smooth tube. Thus, inventors have attempted to create a retractable abrading device which includes a smooth outer tube with an internal retracting component. This allows the user to insert the device into thoracoport 10 without further irritation of the incision site. However, oftentimes these devices are overly complicated. The internal components that retract require mechanical systems and linkages which may malfunction during surgery, thereby further complicating the surgery and/or prolonging the procedure. Therefore, what is needed is an abrading device having a diameter small enough to be inserted into a thoracoport or similarly sized opening.

BRIEF SUMMARY OF THE INVENTION

The present invention comprises an abrading device and method for irritating and blotting a membrane, particularly the pleural membrane. The method uses a device which is small enough to be inserted and withdrawn through a prior art thoracoport. The device includes a proximal end configured to be gripped by a surgeon and a distal end configured to be inserted through a thoracoport into the patient. A stainless steel shaft connects the distal and proximal ends of the abrading device. The distal end includes a series of nylon bristles. The bristles are attached to the device using medical grade stainless steel wire wrapped around the distal end of the device. The connecting shaft and wrapped wire are malleable, thereby allowing the surgeon to adjust the bends within the abrading device prior to insertion into the patient. Preferably, the surgeon can insert the distal end through a thoracoport into the pleural space.

Once the device is inserted, the surgeon grips the proximal end and manipulates the device so that the series of nylon bristles abrades the walls of the pleural space. The shaft of the invention is small enough so that a thoracoscope can remain in the thoracoport with the shaft and be used to observe the abrading process. Once the abrading process is complete, the surgeon can easily withdraw the device back through the thoracoport.

BRIEF DESCRIPTION OF THE SEVERAL VIEWS OF THE DRAWINGS

FIG. 7 is a perspective view, showing the abrading device before it is inserted into a thoracoport.

FIG. 8 is a perspective view, showing abrading device as it Is inserted into a thoracoport, FIG. 9 is a schematic view, showing abrading device within the pleural cavity of a patient.

Figure 1:
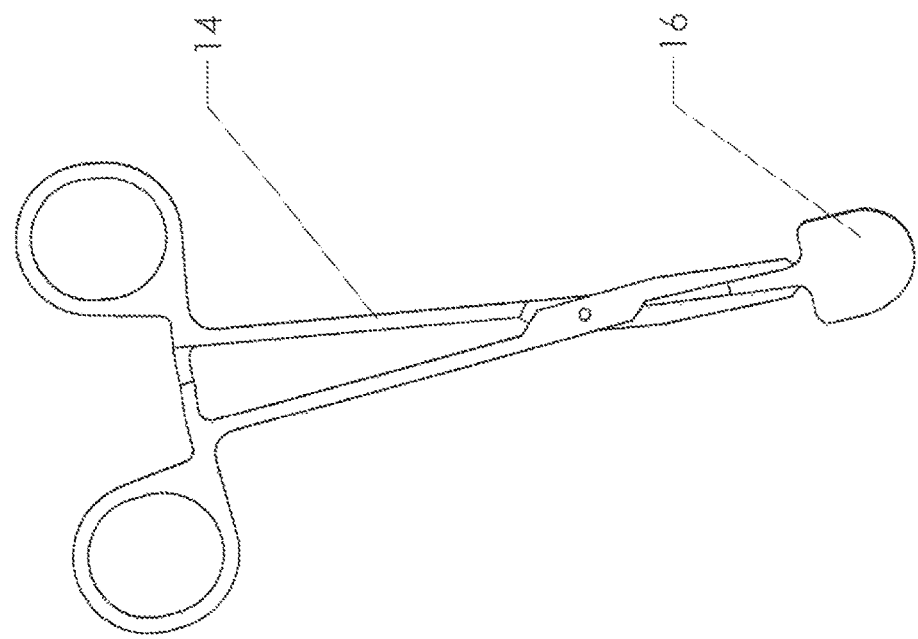
FIG. 1 is a perspective view, showing a prior art Kelly clamp.
Figure 1:
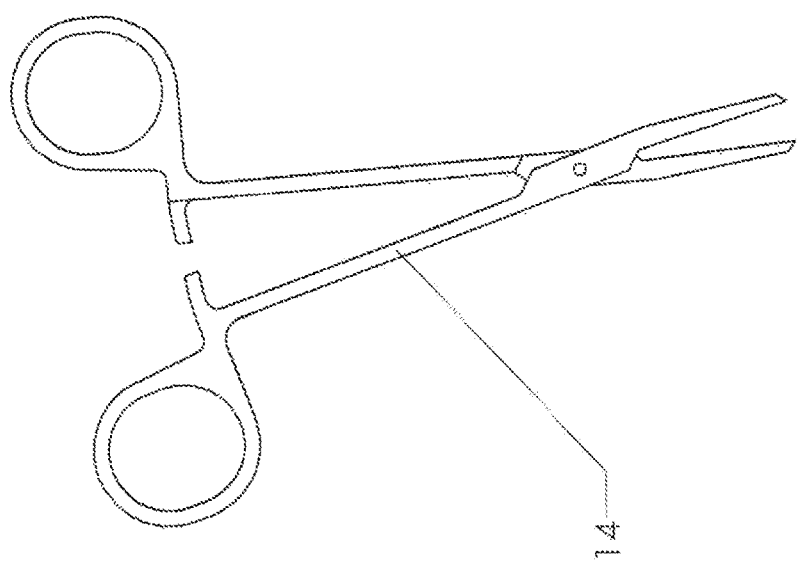
Figure 2:
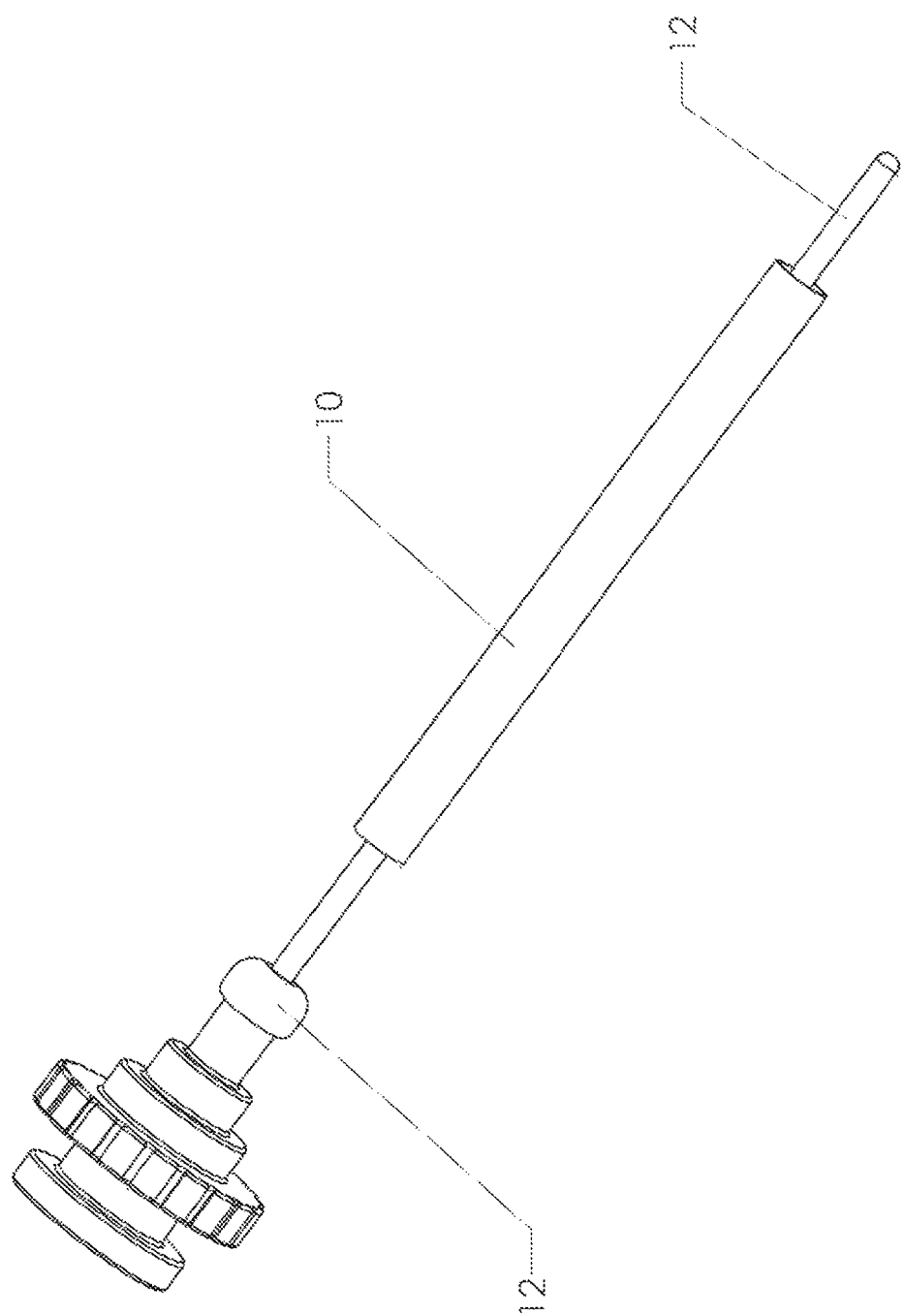
FIG. 2 is a perspective view, showing a prior art thoracoport with prior art thoracoscope inserted therein.

REFERENCE NUMERALS IN THE DRAWINGS 10 thoracoport
12 thoracoscope
14 Kelly clamp
16 gauze
18 abrading device
20 handle
22 shaft
24 abrading end
26 bristles
28 wire
30 tip
32 brush
34 pleural cavity
36 lung
38 visceral pleura
40 parietal pleura

DETAILED DESCRIPTION OF THE INVENTION

Figure 3:
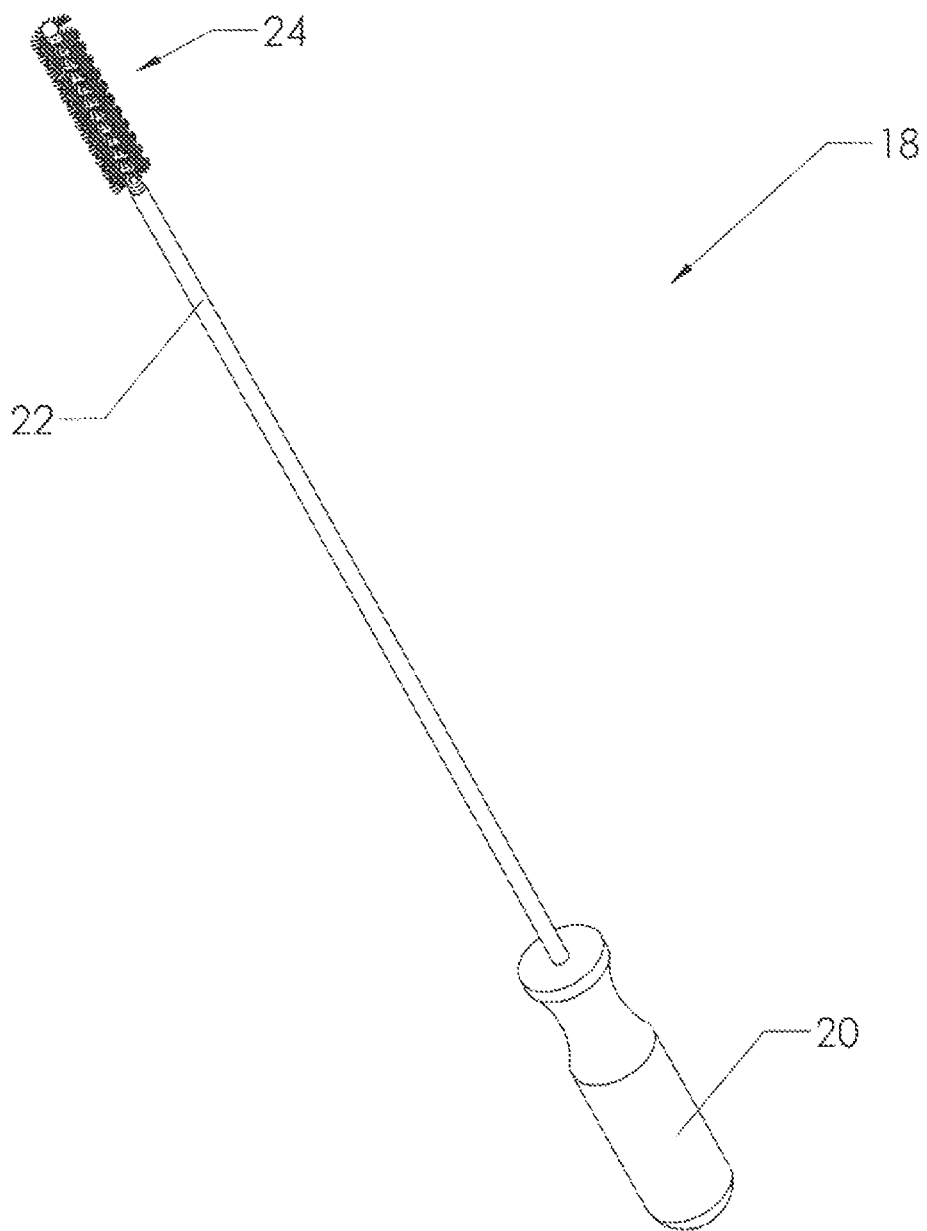
FIG. 3 is a perspective view, showing the abrading device of the present invention.

The present invention is a method and device for abrading the thoracic membrane in a patient during a mechanical pleurodesis surgical procedure. FIG. 3 shows a preferred embodiment of the abrading device used in the present invention. Preferably, abrading device 18 includes handle 20, shaft 22, and abrading end 24. The proximal end of abrading device 18 includes handle 20 and the distal end of abrading device 18 includes abrading end 24. Shaft 22 connects handle 20 to abrading end 24. Preferably, handle 20 is ergonomically designed in order to comfortably fit the hand of a surgeon. Those familiar with the art will realize that this is not a trivial characteristic as a surgeon must be capable of obtaining a firm grip in order to manipulate abrading device 18 within the patient. Shaft 22 is preferably constructed using a surgical grade annealed stainless steel conduit. Those familiar with the art will realize that the term "surgical grade" in relation to stainless steel refers to a corrosive resistant grade of stainless steel. A corrosive resistant material is preferred as the device will be inserted into the thoracic cavity of a patient. In a preferred embodiment of the present invention, shaft 22 is designed in such a way that it is malleable. Those familiar with the art will realize that this depends both on the diameter of shaft 22 and the material. Abrading end 24 comprises multiple materials, which will be discussed further in the following text.

Figure 4:
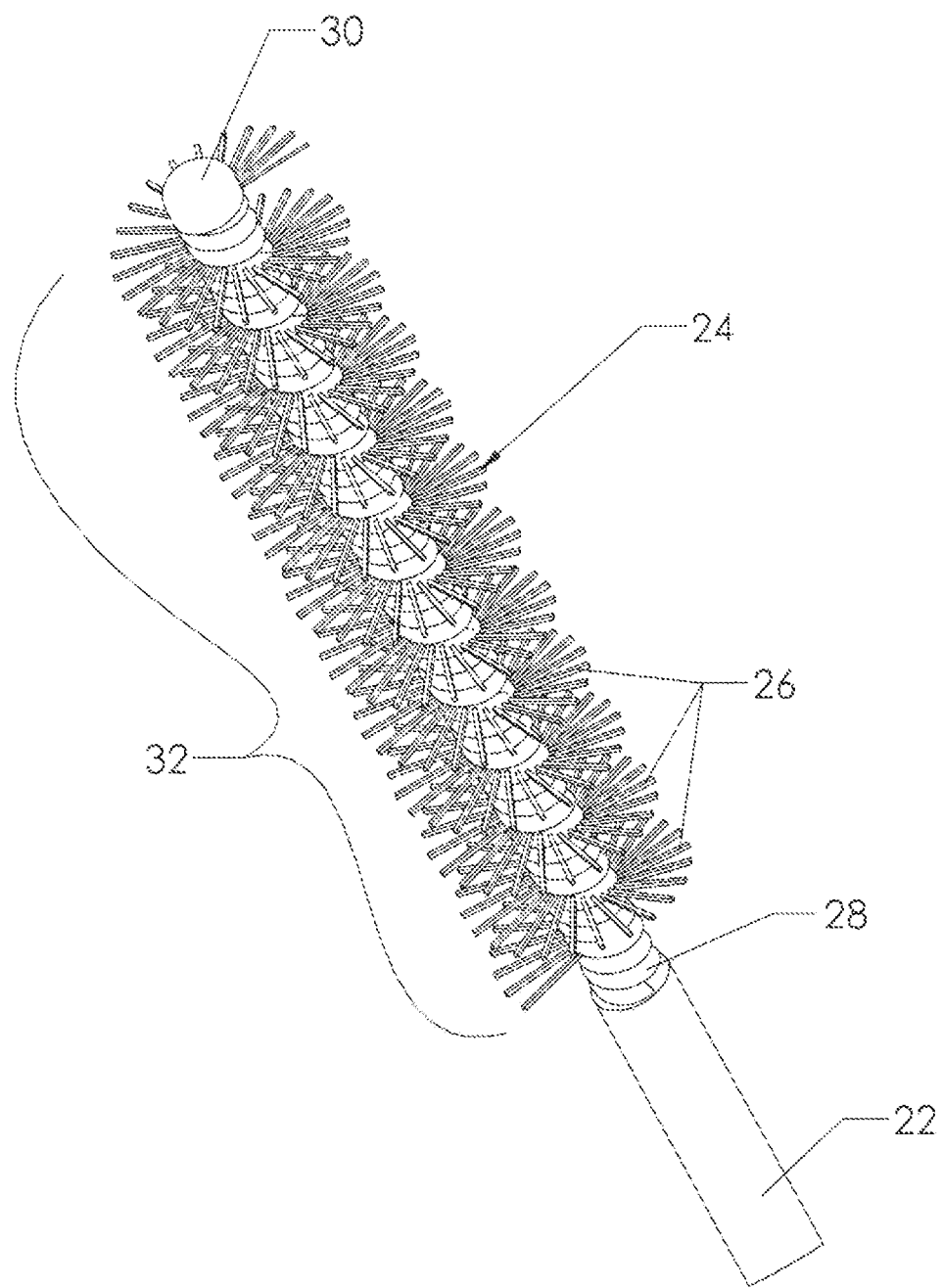
FIG. 4 is a detailed perspective view, showing the brush of the abrading device.

FIG. 4 shows a detailed view of abrading end 24. Preferably, abrading end 24 includes a plurality of bristles 26, wire 28, and tip 30. Preferably, bristles 26 are fabricated using anti-bacterial nylon. Wire 28 is preferably fabricated using surgical grade stainless steel. As illustrated, stainless steel wire 28 is wrapped around nylon bristles 26 in order to keep bristles 26 firmly in place. Wire 28 is wrapped around nylon bristles such that bristles 26 remain in place even while undergoing strong tensile forces. The wrapped bristles 26 form brush 32. Preferably, tip 30 is smooth, and blunt in order to avoid unintentionally puncturing tissues or organs with the distal end of abrading device 18. Of course, bristles 26 can be attached to abrading end 24 using any known method in the art. In addition, a firm polymer or foam attached to abrading end 24 may be used to abrade the pleura of the patient.

Preferably, antibacterial nylon bristles 26 are stiff enough to abrade the pleural membrane of the patient. However, the reader will note that if nylon bristles 26 are too stiff, there is a chance tissue and/or organs can be severed a situation that must be avoided. Thus, the tip 30 of abrading end 24 should also be fabricated in order to avoid puncturing tissue or organs during surgery. Tip 30 is, therefore, preferably fabricated of a smooth, blunt material such as acrylic or a smooth plastic. Of course, tip 30 can take many forms and can be applied using many methods. The advantage of using liquid acrylic applied to tip 30 is the end of abrading end 24 can simply be dipped into liquid acrylic which hardens as it cools/dries, thereby creating a smooth, blunt tip 30. A smooth, blunt tip 30 allows the surgeon to easily traverse abrading device 18 within the patient with little fear of tearing or puncturing tissue and/or organs. In addition, the liquid acrylic bonds securely to the tip 30 of abrading end 24, whereas a material like plastic which would need to be affixed to tip 30 may become dislodged during surgery.

Figure 5:
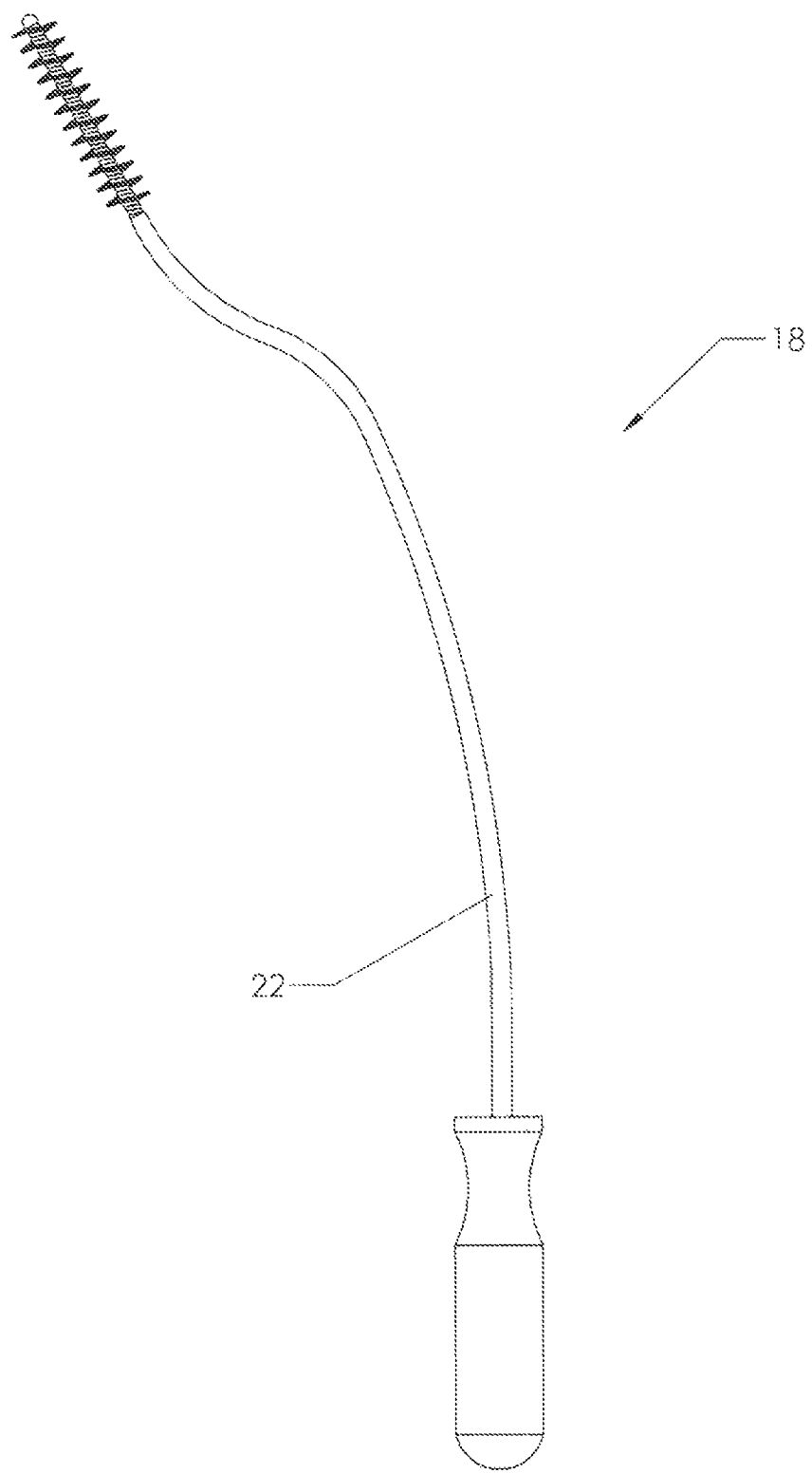
FIG. 5 is a perspective view, showing the abrading device of the present invention with a bent shaft.

In some instances, abrading the patient's pleural membrane may require a device that is not straight. FIG. 5 shows abrading device 18 in a configuration where shaft 22 is bent. Preferably, shaft 22 is fabricated using a surgical grade stainless steel conduit. This allows the surgeon to bend shaft 22 if necessary for insertion. While the material is preferably malleable, shaft 22 should not bend easily. It is important that during surgery, the surgeon can apply a force to shaft 22 without it bending while navigating within the patient's thoracic cavity. In other words, while it is important for the surgeon, to be capable of bending shaft 22, whether it is done manually or using a pipe bending device, shaft 22 should be rigid enough that it does not bend unless the surgeon intends for it to bend. As illustrated, shaft 22 can be bent at varying angles and degrees in three dimensional space.

Figure 6:
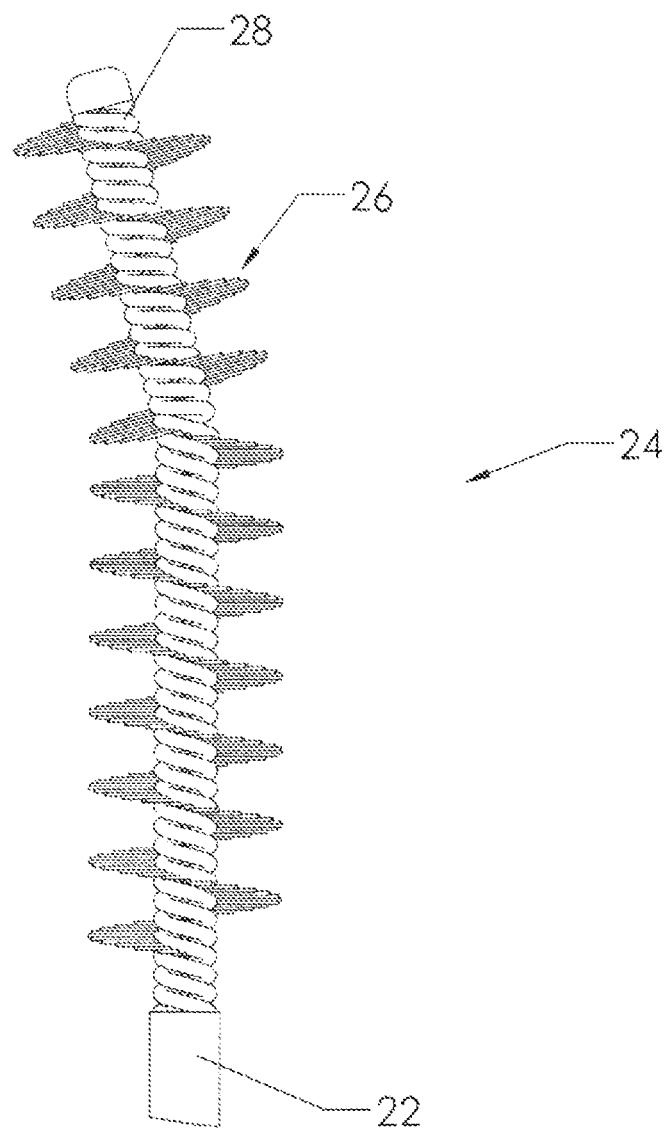
FIG. 6 is a perspective view, showing the abrading end of the abrading device.

FIG. 6 shows a detailed view of abrading end 24 of abrading device 18. As described in the preceding text, abrading tip 24 is fabricated by wrapping stainless steel wire 28 around nylon bristles 26. Those familiar with the art will realize that the wrapped stainless steel wire 28 is malleable. In fact, abrading end 24 is preferably more flexible than shaft 22. As illustrated, abrading end 24 is capable of bending if required by the surgeon. Although it is important that the surgeon can apply a moment to the shaft without the shaft 22 bending, this is less of a concern for abrading end 24 as abrading end 24 is located at the distal end of the device. Similar to shaft 22, abrading tip 24 can be bent by the surgeon based on what he or she needs.

The preceding description and figures have described abrading device 18 in extensive detail. The surgeon can manipulate abrading device 18 in order to conform to the patient's anatomy and the corresponding thoracoport locations. The following description and drawings illustrate the method of using abrading device 18 in order to perform a pleurodesis procedure.

After the surgeon has completed thoracotomy or thoracoscopic surgery, he or she is ready to perform the pleurodesis procedure. Prior to insertion of abrading device 18, the surgeon may need to adjust abrading device 18 to fit the anatomy of the patient. FIG. 7 shows a detailed view of abrading device 18 just before insertion into thoracoport 10. Those familiar with art will realize that thoracoport 10 in an opening in the patient used to perform a thoracoscope surgery. The reader will note that the outer diameter of shaft 20 and the effective outer diameter of wrapped wire 28 is smaller than the inner diameter of thoracoport 10, thereby allowing the surgeon to insert abrading device 18 into thoracoport 10. Although bristles 26 may have an effective outer diameter than the inner diameter of thoracoport, bristles 26 are preferably flexible in the axial direction. Thus, as the surgeon inserts abrading device 18 into thoracoport 10, bristles 26 bend with little resistance. FIG. 8 shows abrading device 18 inserted into thoracoport 10. As abrading device 18 is inserted into thoracoport 10, bristles 26 temporarily bend in order to fit within thoracoport 10. Once bristles 26 enter the pleural cavity, bristles 26 return to their original form.

FIG. 9 shows abrading device 18 within pleural cavity 34. As the surgeon navigates within pleural cavity 34, he or she is careful to avoid the patient's lung 36 and the visceral pleura 38. In order to irritate parietal pleura 40, the surgeon preferably abrades parietal pleura 40 with brush 32. As is typically performed using Kelly clamp 14 and gauze 16, the surgeon performs a pleurodesis using abrading device 18, Once the procedure is complete, the surgeon can easily remove abrading device 18 without irritating the tissue surrounding thoracoport 10.

As discussed in the preceding text, irritation of the tissue surrounding thoracoport 10 during a thoracoscopy is an issue while using a Kelly clamp 14 and gauze 16 to abrade viscera!pleura 38. The abrading device of the present invention is capable of entering and exiting thoracoport without further irritating the tissue surrounding thoracoport 10. In addition, abrading device 18 can be inserted into thoracoport 10 while thoracoscope is within the patient. Thus, the surgeon is able to maintain sight of the target area during pleurodesis. This helps avoid possible complications or inadvertent tearing of tissue.

The preceding description contains significant detail regarding novel aspects of the present invention. It should not be construed, however, as limiting the scope of the invention but rather as providing illustrations of the preferred embodiments of the invention. Thus, the scope of the invention should be fixed by the following claims, rather than by examples given.

Having described my invention, I claim:

1. A method for abrading a membrane located in a patient's body for a thoracic surgical action, said surgical action involving a pleural membrane, a parietal pleura, a pleural cavity, and an opening in said patient's body, comprising:
    a. providing a thoracoport having an inner diameter,
    b. providing an abrading device, including,
        i. a proximal end and a distal end,
        ii. a handle located on said proximal end,
        iii. a brush located on said distal end,
        iv. a shaft connecting said distal end and said proximal end, wherein said shaft has an outer diameter, wherein said outer diameter is smaller than said inner diameter of said thoracoport,
        v. said brush having a plurality of bristles,
        vi. said distal end having a smooth, rounded tip extending distally from the brush;
        vii. wherein said smooth, rounded tip is created using liquid acrylic,
        viii. wherein said thoracoport is independent of said abrading device;
    c. inserting said thoracoport into said pleural cavity by passing said thoracoport through said opening,
    d. inserting said abrading device through said thoracoport;
    e. placing said brush against said parietal pleura in a position where,
        said plurality of bristles rest against said parietal pleura,
        said handle remains outside said patient's body; and
    f. abrading said parietal pleura of said pleural membrane so that said pleural membrane adheres to itself.

2. The method for abrading a membrane located in a patient's body as recited in claim 1, wherein said plurality of bristles fasten to said distal end by wrapping one malleable wire around said plurality of bristles and said distal end.

3. The method for abrading a membrane located in a patient's body as recited in claim 2, wherein said bristles form a helical pattern axially along said abrading device.

4. The method for abrading a membrane located in a patient's body as recited in claim 2, wherein said wire is made of non-corrosive stainless steel.

5. The method for abrading a membrane located in a patient's body as recited in claim 1, wherein said plurality of bristles are made of anti-bacterial nylon.

6. The method for abrading a membrane located in a patient's body as recited in claim 1, wherein said shaft is made of non-corrosive stainless steel.

7. The method for abrading a membrane located in a patient's body as recited in claim 1, wherein said shaft is malleable.

8. A method for abrading a membrane located in a patient's body for a thoracic surgical action, said surgical action involving a pleural membrane, a parietal pleura, a pleural cavity, and an opening in said patient's body, wherein a thoracoport, having a first opening and a second opening, is inserted into said opening in said patient's body, comprising:
   a. providing an abrading device, including,
      i. a proximal end and a distal end,
      ii. a handle located on said proximal end, a brush located on said distal end, and a shaft therebetween,
      iii. said brush having a plurality of bristles,
      iv. said distal end having a smooth, rounded tip extending distally from the brush;
      v. wherein said smooth, rounded tip is created using liquid acrylic,
      vi. wherein said abrading device is independent of said thoracoport;
   b. inserting said abrading device into said thoracoport by passing said distal end into said first opening, such that said brush extends out of said second opening but at least a portion of said shaft remains within said thoracoport;
   c. placing said brush against said parietal pleura in a position where,
      i. said plurality of bristles rest against said parietal pleura,
      ii. said handle remains outside said patient's body; and
   d. abrading said parietal pleura of said pleural membrane so that said pleural membrane adheres to itself.

9. The method for abrading a membrane located in a patient's body as recited in claim 8, wherein:
   a. said plurality of bristles fasten to said distal end by wrapping one malleable wire around said plurality of bristles and said distal end; and
   b. said bristles form a helical pattern axially along said abrading device.

10. The method for abrading a membrane located in a patient's body as recited in claim 9 wherein said wire is made of non-corrosive stainless steel.

11. The method for abrading a membrane located in a patient's body as recited in claim 8, wherein said distal end is dipped into liquid acrylic.

12. The method for abrading a membrane located in a patient's body as recited in claim 11, wherein said liquid acrylic dries in order to create said smooth, rounded tip.

13. The method for abrading a membrane located in a patient's body as recited in claim 8, wherein said plurality of bristles are made of anti-bacterial nylon.

14. The method for abrading a membrane located in a patient's body as recited in claim 8, wherein said shaft is made of non-corrosive stainless steel.

15. The method for abrading a membrane located in a patient's body as recited in claim 8, wherein said shaft is malleable.

* * * * *